United States Patent [19]
Kohno et al.

[11] Patent Number: 5,852,223
[45] Date of Patent: Dec. 22, 1998

[54] PURIFICATION METHODS OF PENTAFLUOROETHANE

[75] Inventors: Satoru Kohno; Takashi Shibanuma, both of Settsu, Japan

[73] Assignee: Daikin Industries, Ltd., Osaka, Japan

[21] Appl. No.: 776,194

[22] PCT Filed: Jul. 25, 1995

[86] PCT No.: PCT/JP95/01488

§ 371 Date: Jan. 28, 1997

§ 102(e) Date: Jan. 28, 1997

[87] PCT Pub. No.: WO96/04226

PCT Pub. Date: Feb. 15, 1996

[30] Foreign Application Priority Data

Jul. 29, 1994 [JP] Japan ...................................... 6-198019

[51] Int. Cl.$^6$ ............................. C07C 17/38; C07C 19/08
[52] U.S. Cl. ......................... 570/178; 570/177; 570/179; 570/180; 570/176
[58] Field of Search ..................................... 570/177, 178, 570/176, 179, 180

[56] References Cited

FOREIGN PATENT DOCUMENTS

| | | |
|---|---|---|
| 3-99026 | 4/1991 | Japan . |
| 4-26636 | 1/1992 | Japan . |
| 1578933 | 11/1980 | United Kingdom ................... 570/176 |

Primary Examiner—Alan Siegel
Attorney, Agent, or Firm—Armstrong, Westerman, Hattori, McLeland & Naughton

[57] ABSTRACT

The purification of pentafluoroethane (HFC-125) which is composed of a process A, in which an unpurified mixture (1), containing at least chloropentafluoroethane (CFC-115) and pentafluoroethane (HFC-125) is reacted with hydrogen (4) in the presence of a catalyst in gas phase to reduce the said chloropentafluoroethane (CFC-115); and a process B, in which a reaction mixture produced by the preceding reaction is separated into a first mixture (3) composed mainly of hydrogen and a second mixture (2), composed mainly of pentafluoroethane (HFC-125). In this method, purification is performed by adding the said first mixture (3) to the said unpurified mixture (1) in a state that the hydrogen chloride is removed from the first mixture (3) in process B until the level of hydrogen chloride drops to 0.5 or less than that of CFC-115 in the unpurified mixture (1) in the molar ratio, or hydrogen chloride is removed from the said reaction mixture until, when mixed with the unpurified mixture (1), the level of hydrogen chloride drops to 0.5 or less than that of CFC-115 in the mixture in the molar ratio.

Thus, CFC-115 can be exterminated (or removed) cheaply and efficiently without decreasing it's reactivity (or activity) and a high yield of HFC-125 can be obtained.

9 Claims, 1 Drawing Sheet

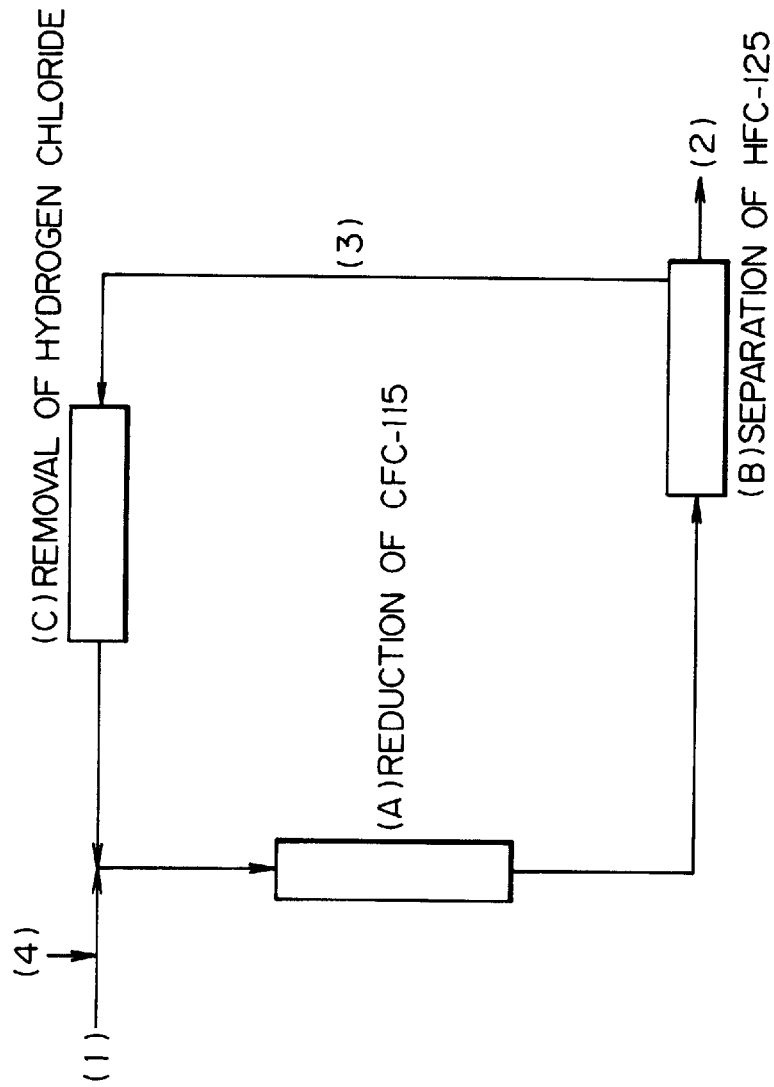

PURIFICATION METHODS OF PENTAFLUOROETHANE

This application is a 371 of PCT/JP95/01488 filed Jul. 25, 1995.

Industrial Fields Where the Invention can be Utilized

This invention relates to purification methods of pentafluoroethane (also referred to as HFC-125), specifically to a method of purification of HFC-125 from a mixture composed of HFC-125 which contains at least chloropentafluoroethane (also referred to as CFC-115) as a component (that is, an unpurified mixture which contains at least CFC-115 and HFC-125).

Conventional Technologies

HFC-125 is a chlorine-free compound and is a useful alternative to flon (chlorofluorocarbons and hydrochlorofluorocarbons). It is used as a refrigerant, a blowing agent and a propellant.

As a method of producing the HFC-125, a method of fluorinating tetrachloroethylene is considered effective.

In this production method, however, CFC-115 is formed as a by-product. Since the boiling point of CFC-115 is $-38.7°$ C., and close to that of the desired product, HFC-125, $-48.5°$ C., and since the relative volatility of CFC-115 to HFC-125 is near 1, it is difficult to separate them by a distillation method.

Thus, it is necessary to remove CFC-115 by another method. One of such method is to remove CFC-115 by converting it to another compound by a reduction.

Such a reduction of CFC-115 is a known reaction. For example, Jap. Unexamined Pat. Publication Nos. 258632/89 and 29941/92, WO 91/05752 and EP 506525 disclose methods of reducing CFC-115 by hydrogen while using mainly noble metals as catalysts. Furthermore, in WO 94/02439, a method of removing CFC-115 by converting it to HFC-125 through hydrogen reduction of HFC-125 which contains CFC-115 at temperatures between 380° C. and 500° C. in the gas phase (that is, the hydrogen reduction of CFC-115), has been disclosed.

However, in such a hydrogen reduction reaction of CFC-115, the amounts of hydrogen generally used is greater than that of CFC-115. In particular, when HFC-125 which contains CFC-115 is reduced (by the method given in WO 94/02439), the amount of hydrogen greatly exceeds that of CFC-115. Hydrogen is very expensive, and the large amount of hydrogen required in the reduction process increases the cost of obtaining the desired product.

Development of the Invention

To resolve the above-mentioned problem, the re-use of hydrogen was considered. Extensive studies of the re-use by the inventors revealed, however, that recycling gas obtained after removal of HFC-125 after reduction reaction reduces reactivity considerably. This necessitates longer reaction times or higher temperatures to sustain reaction with CFC-115 until the target concentration is reached.

At the same time, if the reaction temperature is raised, the amount of multi-reduced products such as R-134a (1,1,1,2-tetrafluoroethane) or R-143a (1,1,1-trifluoroethane) increases when CFC-115 is reduced, resulting in lower yields of HFC-125. If the reaction time is made longer, both the quantity of catalyst and the volume of the reaction vessel increase, resulting in increased costs for catalysts and equipment.

Purpose of the Invention

The purpose of the invention is to provide a purification method for HFC-125, wherein CFC-115 can be exterminated (or removed) cheaply and efficiently without lowering the reactivity (or activity) on recycling hydrogen to produce HFC-125 in high yield, when HFC-125 containing CFC-115 is reduced with hydrogen in the gas phase.

The Structure of the Invention

As a result of intensive studies on the recycle of gas following reduction in the above-mentioned hydrogen reduction, the inventors found that because of the presence of hydrogen chloride which is produced as a by-product during the reduction of CFC-115 in the recycle gas, it's reactivity falls sharply.

The adverse effect of hydrogen chloride was found not to be caused by an equilibrium reaction. (Therefore, even if hydrogen chloride reacts with HFC-125 under the same conditions, CFC-115 will not be produced.) Rather, it is a catalyst poison of reduction catalysts or an obstruction due to adsorption on CFC-115 reduction catalysts that decreases the activity of the catalysts. Furthermore, because higher proportions of hydrogen chloride to CFC-115 increases the adverse effect, when the concentration of CFC-115 to be reacted is low (when there is little CFC-115 in the HFC-125 to be reduced), its reactivity is markedly lower when even a small amount of hydrogen chloride is mixed.

In order to avoid such decrease in reactivity, the inventors confirmed that if the concentration of hydrogen chloride in the gas is lowered before the reacted gas is recycled, the recycle of the gas can bring about reducion of CFC-115 without lowering reactivity, then reached the present invention.

That is, this invention relates to the purification method of pentafluoroethane (HFC-125) wherein, in the case of purification of the said pentafluoroethane (HFC-125) from an unpurified mixture containing at least chloropentafluoroethane (CFC-115) and pentafluoroethane (HFC-125), the method comprises a process A, in which the chloropentafluoroethane (CFC-115) is reduced by reaction with the said unpurified mixture with hydrogen under a catalyst in the gas phase; a process B, in which thus produced reaction mixture is separated into a first mixture composed mainly of hydrogen, and a second mixture composed mainly of pentafluoroethane (HFC-125); and a process C in which hydrogen chloride is removed from the said first mixture until the quantity of hydrogen chloride becomes to be 0.5 or less than that of chloropentafluoroethane (CFC-115) in the said unpurified mixture in the molar ratio; the first mixture is then added in the said unpurified mixture, and the processes A, B and C are repeated continuously as desired.

According to this purification method, the reaction mixture can be separated into the first and second mixtures by a distillation, or a membrane separation or a pressure swing adsorption method in the process B.

Moreover, this invention also provides a purification method of pentafluoroethane (HFC-125). In the case of purification of the said pentafluoroethane (HFC-125) from an unpurified mixture containing at least chloropentafluoroethane (CFC-115) and pentafluoroethane (HFC-125), the method comprises a process I in which the said chloropentafluoroethane (CFC-115) is reduced in the said unpurified mixture with hydrogen under a catalyst in the gas phase; a process II in which, when added to the said unpurified mixture, hydrogen chloride is removed from thus produced reaction mixture until its quantity becomes 0.5 or less than that of chloropentafluoroethane (CFC-115) in the said unpurified mixture of the molar ratio; and a process III in which the reaction mixture is then separated into a first mixture composed mainly of hydrogen and a second mixture, composed mainly of pentafluoroethane (HFC-125), the first mixture then added to the said unpurified mixture, and the processes I, II, and III are repeated continuously as desired.

In this purification method, a distillation, or a membrane separation or a pressure swing adsorption method can be used to separate the reaction mixture into the first and the second mixture in the process III.

With respect to the above-mentioned purification methods based on this invention, in either of the method using the processes A, B and C or the method having the processes I, II and III and regarding the rate of reduction in concentration of hydrogen chloride; since the higher the concentration of hydrogen chloride, the greater the drop of the reaction rate, it was found that the concentration of hydrogen chloride should be 0.5 or less than that of CFC-115 in molarity for recycled gas, preferably be 0.1 or less in a gas mixture which is to be used in reduction reaction and contains at least CFC-115, hydrogen and HFC-125. Ideally, such mixtures should have a concentration of hydrogen chloride of 0.01 or less in the molar ratio.

That is, in the case of reacting the above-mentioned unpurified mixture under a catalyst with hydrogen in the gas phase, the molar ratio of hydrogen to chloropentafluoroethane (CFC-115) should be 5 to 200 in the above-mentioned unpurified mixture, and preferably 10 to 100. The concentration of hydrogen chloride should not be more than 0.5 that of chloropentafluoroethane (CFC-115) in the molar ratio, preferably 0.1 or less, and even more preferably 0.01 or less.

In this case, in order to reduce the concentration of hydrogen chloride (that is, to remove the hydrogen chloride substantially), this can be done by washing the mixed gas with water, or by using an alkaline solid deacidification agent.

In the purification methods based on this invention, where an unpurified mixture is to react in the gas phase with hydrogen gas, it is preferable to use a palladium and/or rhodium catalyst and to initiate the reaction of the unpurified mixture and hydrogen at temperatures between 180° C. and 350° C. in the presence of a catalyst.

Below we show a flow chart describing an example of the efficient purification methods of HFC-125 based on this invention in FIG. 1.

First, HFC-125 containing CFC-115 passes from (1), and hydrogen passes from (4). A reduction catalyst is filled in the reaction process (A). Reaction temperature differs depending on the type and amount of catalyst used, the amount of CFC-115 and the amount of hydrogen, but is generally between 180° C. and 350° C. As CFC-115 is reduced in the reaction process (A), the reaction mixture that completes process (A) contains practically no CFC-115.

The reaction mixture is then sent to the HFC-125 separation process (B) and separated into a mixture (3), mainly composed of hydrogen, and a mixture (2), mainly composed of HFC-125. In this case, one method of separation can be chosen from a distillation, or a membrane separation, and a pressure swing adsorption (PSA) method.

Furthermore, the mixture (2), which is mainly composed of hydrogen, is mixed with the mixture (1) which is in turn, recycled in the reduction reaction after hydrogen chloride has been removed in the hydrochloric acid removal process (C) until concentration is 0.5 or less than that of CFC-115 in the mixture (1) in mole ratio. A removal method for hydrochloric acid (hydrogen chloride) is selected from such as washing with water, or removal by the use of an alkaline solid deacidification agent.

On the other hand, the mixture (2), which is mainly composed of HFC-125, is turned into a product by rectification and other operations after the separation process (B).

The above-mentioned hydrogen chloride removal process was carried out after the separation process (B), but can also be carried out beforehand. In the latter case, process (C) can be carried out after process (A), followed by process (B). In some cases, it is possible to perform hydrogen chloride removal process after gases from (1), (3) and (4) are mixed and before the reaction process (A). In any case, if the concentration of hydrogen chloride is reduced to 0.5 or less than that of CFC-115 in the molar ratio before the reaction process, the process will be successful.

Further, although the flow rate of each gas can incur various conditions, the molar ratio of the hydrogen to CFC-115 before the reaction process (A) could be at least 5 to 200, preferably 10 to 100, and the molar ratio of the hydrogen chloride to CFC-115 should be 0.5 or less, preferably 0.1 or less, and ideally 0.01 or less.

With respect to the percentage of hydrogen, most is recycled in processes (A), (B) and (C). Thus, the amount of hydrogen to be newly added at (4) should correspond to the amount of CFC-115 and the amount that flows outside the process in (2), after the entire processes reach a stationary state.

Possible Industrial Applications

This invention consists of two processes; one is that an unpurified mixture containing at least chloropentafluoroethane (CFC-115) and pentafluoroethane (HFC-125) is made react with hydrogen in the gas phase under a catalyst to reduce the above-mentioned chloropentafluoroethane (CFC-115); and the other process is that the reaction mixture produced by the reduction is separated into a first mixture composed mainly of hydrogen, and a second mixture composed mainly of pentafluoroethane (HFC-125). Then pentafluoroethane (HFC-125) is purified by adding the above-mentioned first mixture to the unpurified mixture after the hydrogen chloride has been practically removed from the first mixture or from the reaction mixture. The first mixture can be added (that is, the hydrogen can be recycled) after the hydrogen chloride, which decreases the reactivity of the catalyst due to a catalyst poison of the reduction catalyst or a adsorption to catalyst by CFC-115, is substantially removed. Thus, CFC-115 can be exterminated (or removed) cheaply and efficiently without decreasing it's reactivity (or activity), and high yields of HFC-125 can be obtained.

BRIEF EXPLANATION OF FIGURE

FIG. 1 is a flow chart which illustrates an example of the purification methods for HFC-125 based on this invention.

EXPLANATION OF SYMBOLS (1) HFC-125 containing CFC-115
(2) A mixture composed mainly of HFC-125
(3) A mixture composed mainly of hydrogen
(4) Hydrogen
(A) Reduction of CFC-115
(B) Separation of HFC-125
(C) Removal of hydrochloric acid (hydrogen chloride)

EXAMPLES

This invention will be explained in detail in the following examples, making comparisons to other methods, but the applications of the method are not limited to such examples.

Comparative Example 1

A stainless steel reaction tube 15 mm in inside diameter was filled with 10 g of a rhodium catalyst, carried on active carbon by 3 wt. %. Hydrogen, CFC-115 and HFC-125 were passed through the tube at a rate of 45 cc/min., 1.9 cc/min. and 56.1 cc/min. respectively to be reacted at a reaction temperature of 250° C.

Analysis of the product at the outlet of the reaction tube by gas chromatograph did not detect CFC-115. The reaction mixture was then passed through a membrane to separate the HFC-125.

After the HFC-125 was separated, the remaining gas contained hydrogen, hydrogen chloride and HFC-125 at a mole ratio of 90:3.8:6.2.

50 cc/min. of this mixture was added to 1.9 cc/min. CFC-115 and 50 cc/min. HFC-125 and again passed through the stainless steel reaction tube 15 mm in inside diameter which was filled with 10 g of a rhodium catalyst carried on active carbon by 3 wt. %. The mixture was made to react at 250° C.

At the inlet of the reaction tube, CFC-115/(CFC-115+ HFC-125) was 3.4%, while at the outlet of the reaction tube, CFC-115 was not detected.

Examples 2 and 3, Comparative Examples 2 to 5

Reactions were carried out similarly, except that the ratio of CFC-115 to hydrogen chloride in the mixture used in the reaction and the type of catalyst were changed as indicated in examples 2 and 3 in Table-1 based on example 1, and as indicated in comparative examples 2 to 5 in Table-1 based on comparative example 1. The percentages of CFC-115/ (CFC-115+HFC-125) after reduction are shown in the following Table-1.

TABLE 1

|  | Reaction temperature (°C.) | Catalyst | (Unit: CC/min.) | | | | Rate after reaction (Unit: %) CFC-115/(CFC-115 + HFC-125) |
|---|---|---|---|---|---|---|---|
|  |  |  | Hydrogen | Chlorine | CFC-115 | HFC-125 |  |
| Example 2 | 250 | A | 45 | 0.2 | 1.9 | 56.1 | 0 |
| Comparative Example 2 | 250 | A | 43 | 1.8 | 1.8 | 56.3 | 0.3 |
| Comparative Example 3 | 250 | A | 42 | 6 | 1.7 | 56.3 | 1.0 |
| Example 3 | 270 | B | 45 | 0.2 | 1.9 | 56.1 | 0 |
| Comparative Example 4 | 270 | B | 43 | 1.8 | 1.8 | 56.3 | 0.4 |
| Comparative Example 5 | 270 | B | 42 | 6 | 1.7 | 53.3 | 1.1 |

The amount of calalyst is 10 g in all cases.
A: Active carbon carrying rhodium by 3 wt. %.
B: Active carbon carrying palladium by 3 wt. %
CFC-115/(CFC-115 + HFC-125) before reaction is approximately 3% in all cases.

The concentration of CFC-115 at the inlet of the reaction tube was CFC-115/(CFC-115+HFC-125)=3.2%, while the CFC-115 concentration at the outlet of the reaction tube was CFC-115/(CFC-115+HFC-125)=0.3%.

Example 1

A stainless steel reaction tube 15 mm in inside diameter was filled with 10 g of a rhodium catalyst carried on active carbon by 3 wt. %. Hydrogen, CFC-115 and HFC-125 were passed at a rate of 45 cc/min., 1.9 cc/min. and 56.1 cc/min. respectively to be reacted at a reaction temperature of 250° C.

Analysis of the product at the outlet of the reaction tube by a gas chromatograph revealed no CFC-115. The mixture was washed with water to remove the hydrogen chloride and dried. The concentration of hydrogen chloride was 0.1% of the HFC-125 in mole ratio.

The mixture was then passed through a membrane to separate the HFC-125 and hydrogen. The mixture which was separated by the membrane device was composed mainly of hydrogen, and also contained hydrogen chloride and HFC-125 at a mole ratio of 93.6:0.1:6.3.

50 cc/min. of this mixture was added to 1.9 cc/min. CFC-115 and 50 cc/min. HFC-125 and passed through the above-mentioned stainless steel reaction tube 15 mm in inside diameter which was filled with 10 g of a rhodium catalyst carried on active carbon by 3 wt. %. The mixture was made to react at 250° C.

Results show that the reduction of CFC-115 depends greatly on the concentration of hydrochloric acid (hydrogen chloride), and that CFC-115 can be completely removed if the reaction is performed after hydrochloric acid is substantially removed using this invention. On the other hand, the reduction of CFC-115 is inhibited as shown in the comparative examples when the reaction is carried out without removal of hydrochloric acid.

Example 4

A stainless steel reaction tube 15 mm in inside diameter was filled with 10 g of a rhodium catalyst carried on active carbon by 3 wt. %. Hydrogen, CFC-115 and HFC-125 were passed through at a rate of 45 cc/min., 1.9 cc/min. and 56.1 cc/min. respectively to be reacted at a reaction temperature of 250° C.

Analysis of the reaction product at the outlet of the reaction tube by gas chromatograph did not detect CFC-115. The mixture was then passed through a membrane to separate the HFC-125.

After the HFC-125 was separated, the remaining mixture was washed with water and dried. The resulting gas contained hydrogen, hydrogen chloride and HFC-125 at a mole ratio of 93.6:0.01:6.4.

50 cc/min. of the mixture was added to 1.9 cc/min. of CFC-115 and 50 cc/min. of HFC-125 and again passed through the stainless steel reaction tube, 15 mm in inside diameter with 10 g of rhodium catalyst carried on active carbon by 3 wt. %. The mixture was made to react at 250° C.

The percentage of CFC-115 at the inlet of the reaction tube was CFC-115/(CFC-115+HFC-125)=3.4% and CFC-115 was not detected at the outlet of the reaction tube.

Reference Example 1

A stainless steel reaction tube 15 mm in inside diameter was filled with 10 g rhodium catalyst carried on active carbon by 3 wt. %. Hydrogen chloride and HFC-125 were passed through the tube at a rate of 10 cc/min. and 100 cc/min. respectively to be reacted at a reaction temperature of 250° C.

Analysis of the product at the outlet of the reaction tube by a gas chromatograph revealed no CFC-115. The HFC-125 and HCl did not react.

What is claimed is:

1. A process for the purification of pentafluoroethane containing at least chloropentafluoroethane as an impurity, comprising A: reacting said chloropentafluoroethane with hydrogen in the presence of a catalyst in gas phase so as to obtain a reaction mixture consisting of a non-organic mixture consisting essentially of hydrogen and hydrogen chloride and a product consisting essentially of pentafluoroethane;

B: separating said product from said non-organic mixture; and

C: removing said hydrogen chloride from said non-organic mixture until the molar ratio of hydrogen chloride to that of the chloropentafluoroethane in the unpurified mixture is 0.5 or less and recycling said non-organic mixture to the unpurified mixture.

2. The purification method as defined in claim 1, in which the process steps A, B and C are continuously repeated.

3. The purification method as defined in claim 1 or 2, in which the reaction mixture is separated in process step B by distillation.

4. The purification method as defined in claim 1 or 2, in which the reaction mixture is separated in process step B by a membrane separation method.

5. The purification method as defined in claim 1 or 2, in which the reaction mixture is separated in process step B by a pressure swing adsorption method.

6. The purification method as defined in one of claims 1 or 2, in which when the unpurified mixture is made to react with hydrogen in the presence of a catalyst in gas phase, the molar ratio of hydrogen to chloropentafluoroethane is between 5 and 200.

7. The purification method as defined in one of claims 1 or 2, in which when the unpurified mixture is made to react with hydrogen in the presence of a catalyst in gas phase, the concentration of hydrogen chloride is 0.5 or less than that of chloropentafluoroethane in the molar ratio in the said unpurified mixture.

8. The purification method as defined in one of claims 1 or 2, in which in the case of the reaction between the unpurified mixture and hydrogen in gas phase, a catalyst carrying palladium and/or rhodium is used.

9. The purification method as defined in one of claims 1 or 2, in which the unpurified mixture is made to react with hydrogen in the presence of a catalyst at temperature between 180° C. and 350° C.

* * * * *